United States Patent [19]

Alles

[11] Patent Number: 4,775,364
[45] Date of Patent: Oct. 4, 1988

[54] NON RE-USEABLE DISPOSABLE HYPODERMIC SYRINGE

[76] Inventor: Anthony Alles, 1511-10 The Driveway, Ottawa, Ontario, Canada, K2P 1C7

[21] Appl. No.: 71,879

[22] Filed: Jul. 10, 1987

[51] Int. Cl.⁴ .............................................. A61M 5/00
[52] U.S. Cl. .................... 604/110; 604/228
[58] Field of Search ............. 604/110, 111, 228, 218, 604/187, 220

[56] References Cited

U.S. PATENT DOCUMENTS

| | | | |
|---|---|---|---|
| 4,233,975 | 11/1980 | Yerman | 604/110 |
| 4,246,898 | 1/1981 | Travalent et al. | 604/220 |
| 4,562,844 | 1/1986 | Carpenter et al. | 604/228 |

*Primary Examiner*—John D. Yasko
*Attorney, Agent, or Firm*—Burns, Doane, Swecker & Mathis

[57] ABSTRACT

There is described a single use disposable hypodermic syringe which has a hollow cylindrical body closed at its front end and open at its rear end. A hypodermic needle is mounted in the closed end of the barrel eccentrically of the longitudinal axis thereof. Inside the barrel there is an inwardly directed lip extending around the inner circumference of the barrel and spaced from the closed end of the barrel and forming with the closed end, a pocket. A plunger is housed in the barrel and is freely reciprocal therein outside the pocket. The plunger has a resilient piston made of a medical rubber compound at its leading end and a plunger rod extends rearwardly of the piston through, and beyond, the end of the barrel and terminates in a flange to which thumb pressure is applied when administering medication with the syringe. The plunger piston is attached to the plunger rod by means of a breakable connection. When the syringe is used and the plunger is depressed into the barrel on its delivery stroke, the piston is forced over the lip and into the pocket where it is retained by the lip. Any attempt to remove the piston from the pocket by attempted withdrawal of the plunger, so that the syringe may be reused, causes the breakable connection to break between piston and plunger piston rod, thereby rendering the syringe useless.

8 Claims, 1 Drawing Sheet

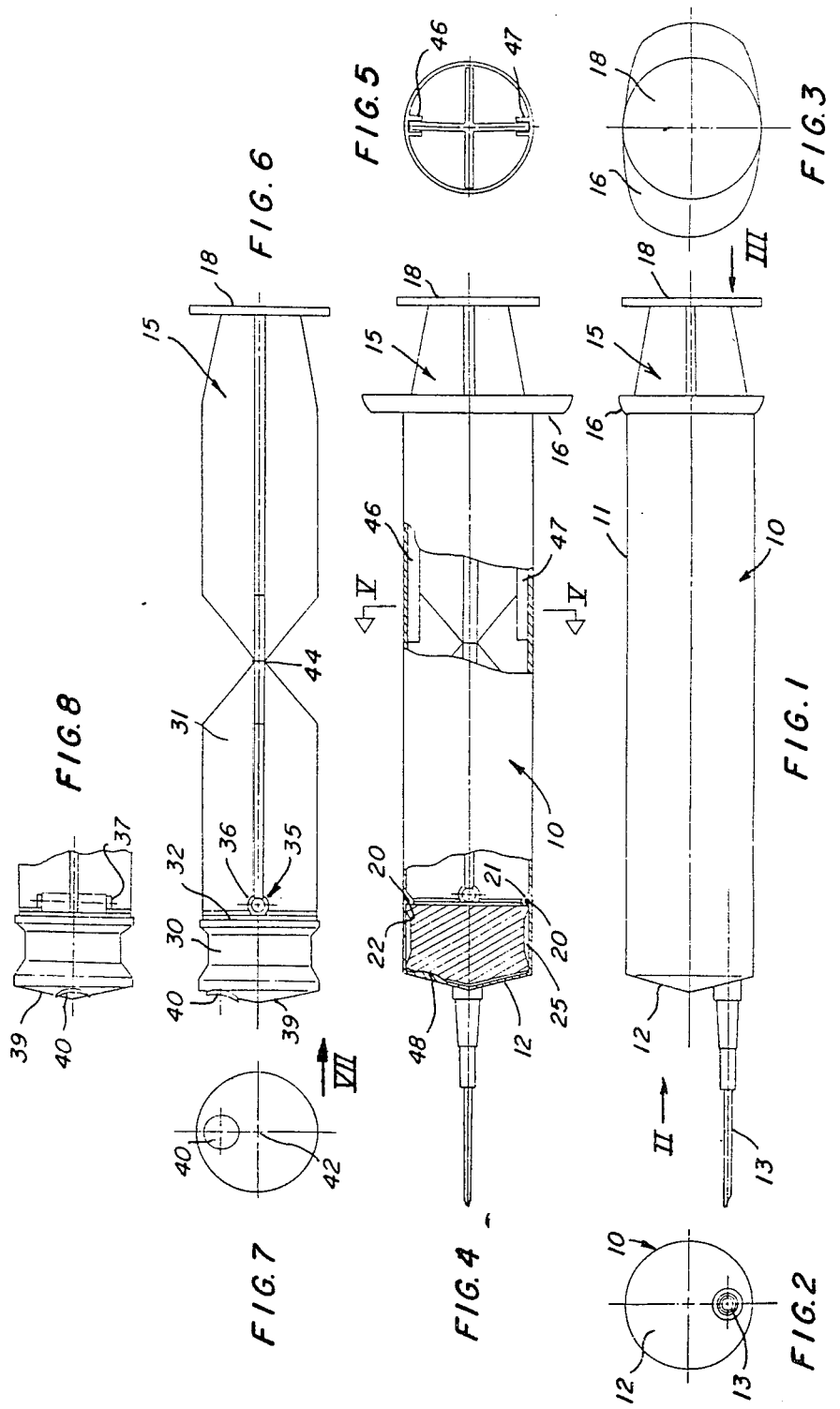

NON RE-USEABLE DISPOSABLE HYPODERMIC SYRINGE

BACKGROUND OF THE INVENTION

The present invention relates to hypodermic syringes for administering medication and more particularly to non-reusable or single use, disposable hypodermic syringes.

There are many situations in which after the administration of medication by a hypodermic syringe, the hypodermic syringe should be destroyed because to reuse it may involve the spread of infection. In these circumstances single use disposable syringes are used. However, particularly in third world countries, single use syringes are often reused although they are clearly marked for disposal.

It is an object of the present invention to provide a single use hypodermic syringe which, because of its very construction, is impossible to reuse, after it has been used once.

According to the present invention there is provided a single use disposable hypodermic syringe comprising a hollow cylindrical barrel closed at its front end by a wall, a hypodermic needle mounted in said wall and in fluid communication with the inside of the barrel, an inwardly directed lip means within the barrel extending over at least part of the inner circumference thereof and spaced longitudinally inwardly from the wall to form a pocket therebetween in the barrel, a plunger housed within the barrel and being freely reciprocable therein outside of the pocket, the plunger having piston means of resilient material at the leading end thereof and a plunger rod means extending longitudinally of, within, and beyond, the barrel, and frangible connections between the piston means and the plunger rod means, whereby in operation the plunger on its delivery stroke forces the piston means into the pocket where it is retained by the lip means, any attempt to remove the piston means from the pocket by attempted withdrawal of the plunger, causing the frangible connections to break.

In a preferred form of the invention the piston means has a suction cup means on its leading face and the wall has a co-operating dome member formed on its inner face. Preferably the hypodermic needle, cup means and dome member are positioned eccentrically of the central axis of the syringe.

It is preferred that the frangible connection be immediately behind a flat rear face of the piston means.

According to a feature of the invention the plunger rod has an area of reduced cross section to provide a fracture point and preferably the plunger rod is of cruciform cross section.

Guideways may be provided on the inside of the barrel to engage the plunger rod and prevent its rotation within the barrel. The guideways may extend longitudinally of the barrel near its outer end and for less than half the length of the barrel.

According to a preferred construction the frangible connections comprise a pin on the plunger rod extending transversely of the barrel and received in substantially semi-cylindrical socket arranged transversely at the rear of the piston means. Suitably the piston means may be made of a medical rubber compound and the lip may span the entire inner circumference of the barrel.

BRIEF DESCRIPTION OF THE DRAWINGS

The following is a description by way of example of an embodiment of the present invention reference being had to the accompanying drawings in which:

FIG. 1 is a side elevation of the hypodermic syringe shown in the condition following the delivery of a dose of medication;

FIG. 2 is an end view looking in the direction of the arrow II in FIG. 1;

FIG. 3 is an end view looking in the direction of the arrow III in FIG. 1;

FIG. 4 is a plan view, partially in section of the hypodermic syringe shown in FIG. 1;

FIG. 5 is a section on the line V looking in the direction of the arrows in FIG. 4;

FIG. 6 is a plan view of the piston removed from the hypodermic syringe of FIGS. 1 and 4;

FIG. 7 is an end view looking in the direction of the arrow VII in FIG. 6; and

FIG. 8 is a detail in elevation of the leading end of the plunger of FIG. 6.

DESCRIPTION OF THE PREFERRED EMBODIMENTS

Turning now to the drawings a hypodermic syringe 10 comprises a hollow cylindrical barrel 11 preferably made of a suitable plastic material, closed at the front by an end wall 12 which carries a hypodermic needle 13. The needle 13 in fluid communication with the inside of the barrel 10. Received within the barrel 11 is a plunger 15 of cruciform section (best seen in FIG. 5). The plunger is also preferably made of a suitable plastic material. The barrel 11 has an outer flange 16 of conventional construction and the plunger 15 terminates in a head 18. In normal operation when delivering medication the flange 16 is held between the first and index finger of the operator whilst pressure is applied to the head 18 by the thumb.

As best seen in FIG. 4 an inwardly directed lip, or protuberance, 20 is molded into the inner surface of the barrel 11 and preferably extends completely around the inner circumference of the barrel. As shown the lip 20 has a tapered outer surface 21 and an abrupt flat inner surface 22. The lip is spaced longitudinally inwardly from the end wall 12 and forms therewith a pocket 25.

As best seen in FIGS. 6 and 8 the plunger 15 carries at its leading end a piston 30 made of resilient material, preferably a medical rubber compound. The plunger 30 is dimensioned so that it may fit snugly within the pocket 25.

Part of the plunger 15 is a plunger rod 31 which is connected to a flat rearface 32 of the piston 30 by means of a frangible connection 35. As seen in FIG. 8, the rear face 32 of the piston has molded thereon a semi-cylindrical socket 36 which receives a pin 37 which extends transversely of the plunger 15 and is molded thereto. At the leading face 39 of the piston 30 there is provided a suction cup 40 positioned eccentrically of the central axis 42 of the syringe.

As best seen in FIG. 6, the plunger rod 31 of the plunger 15 is provided with an area of reduced cross section 44 and, as best seen in FIGS. 4 and 5 the cruciform section plunger 15 is guided in molded guideways 46, 47 which prevents rotation of the plunger. The guidways extend into the barrel 11 from its open end for somewhat less than half the barrel length.

A raised domed portion 48 (FIG. 4) is provided on the inner face of the end wall 12 and is positioned eccentrically thereon so as to mate with the suction cup 40 on the leading face 39 of the piston 30.

The plunger 15 and piston 30 are arranged within the barrel 40 with the plunger 15 extending beyond the end flange 16 of the barrel and the plunger 15 and piston 30 are free to reciprocate in the guides 46,47 within the barrel outside the pocket 25.

In operation the needle 13 is inserted into the vial of medication to be used and the plunger 15 is moved outwardly of the barrel 11 causing the piston 25 to create a sucking action within the barrel drawing medication thereinto. After charging, the piston is moved forwardly to expel excess air from the barrel of the syringe and any excess medication until the desired dosage is arrived at, in the usual fashion. The hypodermic needle is then inserted into the patient's body and by pressure on the head 18 the piston is forced forwardly in the barrel of the syringe to expel the medication through the needle 13. As the piston 30 engages the sloping faces 21 of the lip 20, the resilient rubber of the piston gives way and the piston 30 is forced into the pocket 25 hard up against the inner surface of the wall 12 so that all medication is expelled. The piston 30 is now trapped within the pocket by the flat surfaces 22 of the lip 20 and further the suction cup 40 engages the dome 48 and seals itself thereto.

The useful life of the syringe is now expired and it may be disposed of in the normal fashion. However should a user attmpt to reuse the hypodermic syringe it will be found that any attempt to withdraw the plunger 15 from the barrel 10 will be resisted by the action of the lip 20 on the piston 30 and the action of the suction cup 40 on the dome 48. If an attempt is made to force the piston 25 back out of the pocket, the rod 37 will simply be pulled out of its semi-cylindrical socket 36 causing the connection to fracture. The plunger 15 is then uselessly withdrawn from the barrel 11 which is completely sealed at its front end by the piston 30 and the syringe is incapable of reuse. Because of the guides 46 and 47 it is not possible to attempt to withdraw the piston by adding a rotation to the plunger and should the rod 37 and socket 36 jam for any reason, continued attempt to remove the plunger 15 will cause failure of the plunger rod 31 at the fracture point 44 and the outer part of the plunger will be withdrawn, uselessly.

It will be understood of course that certain modifications are possible. For example the piston 30 could be provided with a rearwardly extending stub rod to which the frangible connection 35 could be attached to connect the piston 30 to the plunger rod 31, or extra guideways could be provided for the other arm of the cruciform plunger, or the fracture point 44 could be obtained by reducing the cross-section of the plunger piston rod 31 in a different fashion, or the location of rod 31 and socket 36 could be reversed, or the shape of the protruberance or lip could be altered, and so on.

The embodiments of the invention in which an exclusive property or privilege is claimed are defined as follows:

1. A single use disposable hypodermic syringe comprising a hollow cylindrical barrel closed at its front end by a wall, a hypodermic needle mounted in said wall and in fluid communication with the inside of said barrel, an inwardly directed lip means within the barrel extending over at least part of the inner circumference thereof and spaced longitudinally inwardly from said wall to form a pocket therebeween in said barrel, a plunger housed within said barrel and being freely reciprocable therein outside of said pocket, said plunger having a piston means of resilient material at the leading end thereof, suction cup means on the leading face of said piston means, a dome means adapted to cooperate with said suction cup means, formed on the inner face of said wall, said plunger having a plunger rod means extending longitudinally of, within, and beyond, said barrel, and frangible connections between said piston means and said plunger rod means, whereby in operation the plunger on its delivery stroke forces said means into said pocket where it is retained by said lip means, any attempt to remove said piston means from said pocket by attempted withdrawal of said plunger, causing said frangible connections to break.

2. A syringe as claimed in claim claim 1 wherein said piston means has a suction cup means on its leading face and said wall has a cooperating dome member formed on its inner face.

3. A syringe as claimed in claim 1 wherein said hypodermic needle, said cup means and said dome member are positioned eccentrically of the central axis of said syringe.

4. A syringe as claimed in claim 1 in which said frangible connections comprises a pin on said plunger rod extending transversely of said barrel and received in a substantially semi-cylindrical socket arranged transversely at the rear of said piston means.

5. A single use disposable hypodermic syringe comprising a hollow cylindrical barrel closed at its front end by a wall, a hypodermic needle mounted in said wall and in fluid communication with the inside of said barrel, a plunger housed within said barrel and being freely reciprocable therein, said plunger having piston means of resilient material at the leading end thereof, suction cup means on a leading face of said piston means, a suction cup co-operation dome member formed on the inner face of said wall, said plunger having a plunger rod means extending longitudinally of, within, and beyond, said barrel, and frangible connections between said piston means and said plunger rod means, whereby in operation the plunger on its delivery stroke forces said suction cup on said piston means into engagement with its co-operating dome member, any attempt to withdraw said piston means and disengage said suction cup means, causing said frangible connections to break.

6. A syringe as claimed in claim 5 wherein said hypodermic needle, said cup means and said dome member are positioned eccentrically of the central axis of said syringe.

7. A syringe as claimed in claim 5 in which said frangible connections comprises a pin on said plunger rod extending transversely of said barrel and received in a substantially semi-cylindrical socket arranged transversely at the rear of said piston means.

8. A single use disposed hypodermic syringe comprising a hollow cylindrical barrel closed at its front end by a wall, a hypodermic needle mounted in said wall and in fluid communication with the inside of said barrel, a plunger housed within said barrel and being freely reciprocable therein, said plunger having piston means of resilient material at the leading end thereof, suction means on a leading face of said piston means, a suction means co-operating raised means formed on the inner face of said wall, said plunger having a plunger rod means extending longitudinally of, within, and beyond, said barrel, and frangible means on said plunger rod means, whereby in operation the plunger on its delivery strode forces said suction means on said piston means into engagement with its co-operating means, any attempt to withdraw said piston means and disengage said suction means, causing said frangible means to break.

* * * * *